United States Patent [19]

Irnich et al.

[11] 4,129,133
[45] Dec. 12, 1978

[54] INTERFERENCE-DETECTING DEMAND HEART PACEMAKER

[76] Inventors: Werner Irnich, Reimser Str. 48, 51 Aachen, Germany; Jacques de Bakker, Morettistr. 54, Vaals, Netherlands

[21] Appl. No.: 774,326

[22] Filed: Mar. 4, 1977

[30] Foreign Application Priority Data

Jun. 25, 1976 [DE] Fed. Rep. of Germany ....... 2628629

[51] Int. Cl.$^2$ .............................................. A61N 1/36
[52] U.S. Cl. .............................................. 128/419 PG
[58] Field of Search ............................... 128/419 PG

[56] References Cited

U.S. PATENT DOCUMENTS

| | | | |
|---|---|---|---|
| 3,949,759 | 4/1976 | Brownlee et al. | 128/419 PG |
| 3,972,334 | 8/1976 | Wickham | 128/419 PG |
| 3,985,142 | 10/1976 | Wickham | 128/419 PG |
| 4,023,121 | 5/1977 | Alley | 128/419 PG |
| 4,043,347 | 8/1977 | Renirie | 128/419 PG |

*Primary Examiner*—William E. Kamm
*Attorney, Agent, or Firm*—Ernest F. Marmorek

[57] ABSTRACT

A heart pacemaker for generating a heart stimulation signal in the apparent absence of any heart stimulation signal during a given duration of time, includes an interference detecting device for sensing intracardiac voltage signals which generate, respectively, first and second signals.

A retriggerable monostable first multivibrator is responsive to a trigger signal, so as to determine a first period of time, and, a second multivibrator is coupled to the first multivibrator, so as to operate for initiating a second period of time; the appearance of the second signals inhibits the heart stimulation signal; the first signal is generated in response to the sensing of one of the intracardiac voltage signals, and the second signals are generated whenever one of the intracardiac voltage signals is not succeeded by another voltage signal during the predetermined first period of time.

A generating device coupled to the detecting means may be operated for generating the heart stimulation signal at the completion of the occurrence of one of the second signals and may be operated to have the second period of time interrupted in response to the occurrence of a further one of the second signals.

3 Claims, 4 Drawing Figures

INTERFERENCE-DETECTING DEMAND HEART PACEMAKER

BACKGROUND OF THE INVENTION.

The invention relates to a heart pacemaker for generating a heart stimulation signal in the apparent absence of any heart stimulation signal during a given duration of time.

Generally, a demand heart pacemaker includes a detecting device for sensing and recognizing the occurrence of intracardiac voltage signals, and an interference recognition device for evaluating the intracardiac voltage signal senses to determine if it is an interference signal, and a signal generator operable to generate the heart stimulation signal a predetermined period of time after the sensing of a signal recognized as having the characteristics of heart stimulation signals.

Prior art demand heart pacemakers generally include an interference recognition device which distinguishes noise signals from heart stimulation signals by the fact that noise signals are repetitious. A typical prior art interference recognition device is described in the German Patent BD-AS 2,025,499 and includes a circuit comprising a capacitor arranged to have two discharge time constants, one by a discharge due a first resistor and the second one by discharge between a series arrangement of a diode and a second resistor. The first time constant is selected to be considerably greater than the second time constant.

The prior art interference recognition devices for heart pacemakers have presented many problems because they have difficulty in distinguishing many types of interference signals such as an interference signal lasting for a short time duration or one that is periodic or one that has an amplitude modulation within the physiological range. In addition, the prior art interference recognition devices cannot determine an interference signal at the early stages of the occurrence of the interference signal.

As a result of these deficiencies, the prior art heart pacemakers often erroneously identify an interference signal as being an acceptable intracardiac voltage signal and no heart stimulation signal is generated by the pacemaker. This loss of a heart stimulation signal creates a dangerous situation for the pacemaker patient.

Generally, interference signals of the type that can interfere with a heart pacemaker are commonplace everyday events. For example, the operation of push buttons for control devices can generate interference signals. Periodic closure of such push buttons can potentially interfere with the useful operation of prior art pacemakers. Interference signals can arise from electrotherapeutical equipment which can generate voltage signals similar in waveform to heart stimulation signals. In addition, inductively coupled interference voltages can occur in everyday life in a form of pulsed signals or amplitude modulated signals due to an electric arc welder or an electric melting furnace, particularly at the outset of operations.

The instant invention is an improved heart pacemaker due to the improved recognition of interference signals, particularly at their initial stages.

SUMMARY OF THE INVENTION

One of the principal objects of the invention is a heart pacemaker for generating a heart stimulation signal in the apparent absence of any heart signal during a given duration of time and includes interference detecting means operable for sensing intracardiac voltage signals possessing predetermined voltage waveform properties and operable for generating, respectively, first and second signals, the first signals being generated in response to the sensing of one of the intracardiac voltage signals by the detecting means and the second signals being generated whenever one of the intracardiac voltage signals is not succeeded by another voltage signal during a predetermined first period of time thus indicating that the first signals were not generated by interference signals, and generating means coupled to the detecting means and operable for generating the heart stimulation signal at the completion of a predetermined second period of time subsequent to the occurrence of one of the second signals and operable to have the second period of time interrupted in response to the occurrence of one of the second signals indicating that the first signals were produced by an action of the heart itself.

Further objects and advantages of the invention will be set forth in part in the following specification and in part will be obvious therefrom without being specifically referred to, the same being realized and attained as pointed out in the claims hereof.

The invention accordingly comprises the combination of elements and arrangements of parts which will be exemplified in a construction hereinafter set forth and the scope of the application of which will be indicated in the claims.

BRIEF DESCRIPTION OF THE DRAWINGS.

For a fuller understanding of the nature and objects of the invention, reference should be had to the following detailed description, taken in connection with the accompanying drawings, in which.

DESCRIPTION OF THE PREFERRED EMBODIMENT

Figure 1:
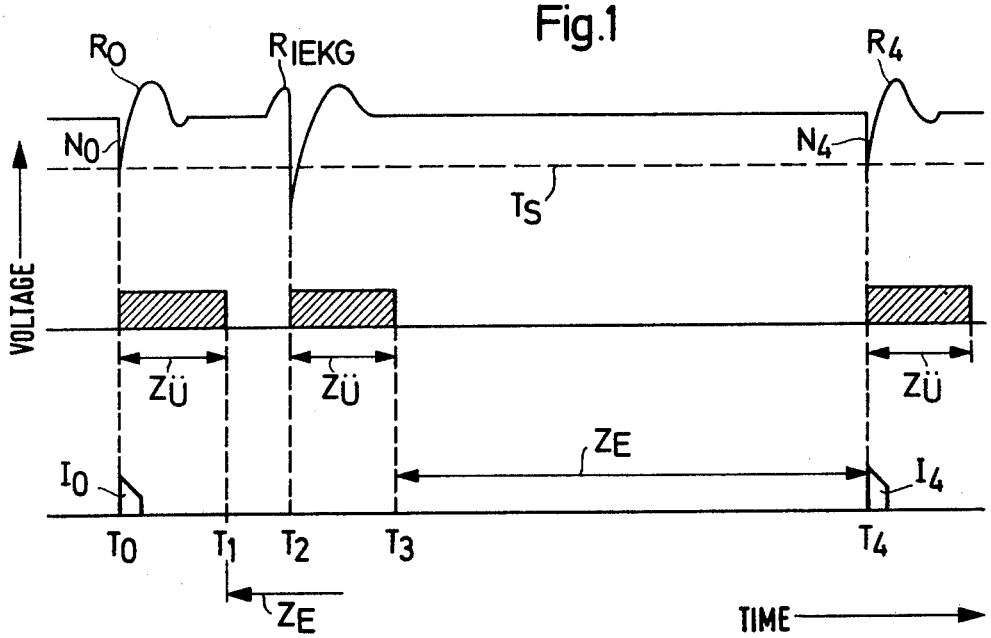
FIG. 1 shows curves illustrating the mode of operation of the instant invention.

To carry the invention into effect, one of the embodiments has been selected for illustration in the accompanying drawings and for description in this specification, reference being had to the FIGS. 1 to 4.

Generally, the instant invention makes use of the fact that an intracardiac voltage signal can be amplified and processed to derive a single voltage signal corresponding to the QRS complex. For example, it is known that the intracardiac unipolar EKG begins with a more or less distinctly formed positive spike or peak which is followed by a sharp negative slope and this is followed by oscillations possessing a low frequency and small amplitudes. The oscillations terminate after about 250 to 350 milliseconds.

Thus, if within a short monitoring period of time, only a single negative spike is detected, there is a high probability that the signal was produced by an action of the heart itself. The occurrence of multiple spikes within a short monitoring period of time would infer the presence of interference signals. This forms the basis for the instant invention.

Generally, experiments tend to suggest that for the instant invention the upper limit for the length of time for monitoring cardiac voltage signals is about 200 milliseconds. This approximate upper limit is based on experiments which show that a monitoring period of time greater than 200 milliseconds can cause complications in patients who have tachycardiac heart rhythm disturbances.

In addition, a longer monitoring period of time does not take into account the fact that practically no interference signal is likely to occur which does not possess at least several spikes or oscillations within a 200 milliseconds interval.

The lower limit for monitoring the cardiac voltage signals can be derived from the lowest frequency of the possible interference signals. For example, if alternating current at the common household frequency of 60 Hertz is a possible interference signal, then it can be easily calculated that the possible interference peaks can occur in an interval of about 16.6 milliseconds. From a practical point of view, a monitoring period of about 16.6 milliseconds is insufficient to detect interference signals with a high probability. Increasing the monitoring period to at least 1.5 times the period of the lowest expected interference signal substantially increases the likelihood of identifying an interference signal. For an expected interference signal having a frequency of 60 Hertz this gives a lower limit of 25 milliseconds for the monitoring.

If the possible interference signal has a frequency of 50 Hertz, similar calculations give a suggested lower limit for the monitoring period to be about 30 milliseconds. Similarly, if the interference signals could have a frequency of about 16⅔ Hertz, then the lower limit for the suggested monitoring period should be about 90 milliseconds.

It has been determined that a monitoring time interval of from about 120 to about 150 milliseconds is preferred in order to detect with a high probability interference signals having very low frequencies.

FIG. 1 illustrates a case in which a spontaneous heart action occurs during a monitoring time period. The events in the FIG. 1 are as follows:

At time $T_o$, a pulse signal $I_0$ is generated within the instant pacemaker and triggers the generation of a heart stimulation signal $R_o$. The negative peak $N_o$ falls exceeds in absolute magnitude a predetermined threshold $T_S$ and is detected as being a possible heart stimulation signal. Thereafter, a monitoring interval $Z_{\ddot{u}}$ is commenced which corresponds to the first period of time and has a duration of about 120 milliseconds. No additional voltage signal having a negative peak below $T_S$ is detected during this period $Z_{\ddot{u}}$. Thus, the instant circuit classifies the signal $R_o$ as being a heart stimulation signal and then commences a second period of time, the so-called demand period of time which lasts for a period of $Z_E$. At time $T_2$, a cardiac voltage signal $R_{IEKG}$ is detected as having a negative peak going below the threshold $T_S$. This new signal interrupts the demand period $Z_E$ and initiates a new monitoring period $Z_{\ddot{u}}$. During this new monitoring period, no additional trigger signal is sensed and this is taken to be an indication that the signal sensed at time $T_2$ was actually created by an EKG signal. At the end of this monitoring period $Z_{\ddot{u}}$, the second signal is generated at time $T_3$ to initiate the demand period $Z_E$. Thus, the determination of whether a signal is a result of heart action is delayed by the time $Z_{\ddot{u}}$.

During the time interval $Z_E$ as shown in the FIG. 1, no additional trigger signal is sensed and at time $T_4$, a pulse signal $I_4$ is generated. The pulse signal $I_4$ initiates the generation of the stimulation pulse signal $R_4$. The negative spike $N_4$ initiates the monitoring period $Z_{\ddot{u}}$ as shown.

Figure 2:
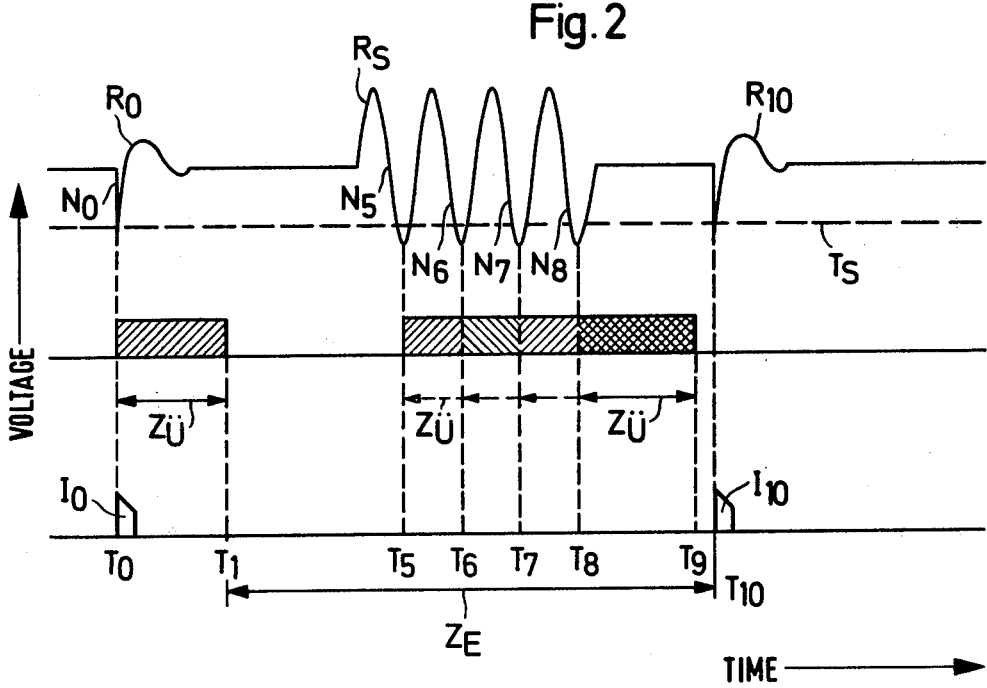
FIG. 2 shows additional curves illustrating the mode of operation of the instant invention.

The FIG. 2 shows the same operating sequence as FIG. 1 up to the time $T_1$. At time $T_5$, an interference signal $R_S$ having four oscillations is detected and these oscillations have a repetition period smaller than the time interval $Z_{\ddot{u}}$. The negative-going half wave $N_5$ initiates the monitoring period $Z_{\ddot{u}}$ and the subsequent detection of the negative-going half wave $N_6$ inhibits the initiation of the demand period $Z_E$. The negative-going half wave $N_6$ itself initiates a monitoring period $Z_{\ddot{u}}$, but the occurrence of the negative-going half wave $N_7$ at time $T_7$ interrupts this period and initiates a new monitoring period $Z_{\ddot{u}}$. At time $T_8$, the occurrence of the negative-going half wave $N_8$ interrupts the monitoring period to start a new monitoring period. This monitoring period is concluded at time $T_9$. At time $T_{10}$, the demand interval $Z_E$ initiated at the time $T_1$ ends and a pulse signal $I_{10}$ is generated to produce the generation of a stimulation pulse at the stimulation electrode (not shown). The occurrence of this stimulation pulse signal initiates a new monitoring period $Z_{\ddot{u}}$ and the cycle of events continues.

Figure 3:
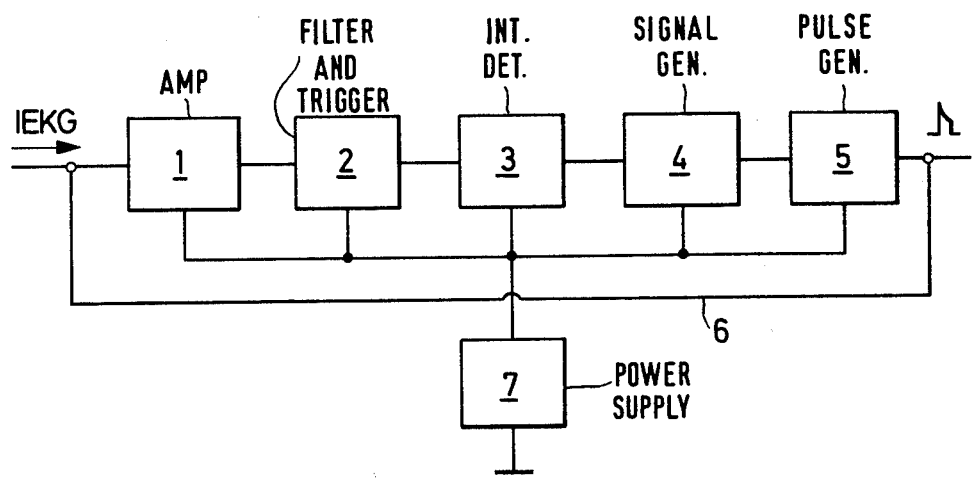
FIG. 3 shows a block diagram of one embodiment of the instant invention.

FIG. 3 shows a preferred embodiment of the instant pacemaker. An intracardiac voltage signal IEKG is sensed by interference detecting means including amplifier 1, filter and trigger device 2, and interference detector 3. Generally, the amplifier 1 amplifies by about 500-fold. The filter and trigger device 2 includes a bandpass filter and generates a pulse signal which is coupled to the interference detector 3. The interference detector 3 determines if the sensed signal is a spontaneous heart signal or an interference signal.

Generating means including signal generator 4 which consists of a timing circuit responsible for the second period of time $Z_E$ and pulse generator 5 is coupled to the interference detector 3 and is responsive to signals generated by the interference detector 3. In the case of a sensed spontaneous heart signal, the signal generator 4 is inhibited for the demand period $Z_E$. If, at the end of the demand period, no additional spontaneous heart signal is sensed, the pulse generator 5 generates a heart stimulation pulse signal which is coupled through lead 6 a stimulation electrode, to bring about an artificially induced contraction of the heart muscle. Generally, the same electrode is used for both sensing and intracardiac voltage signals and supplying a heart stimulation signal. A power supply 7 such as a battery is used to supply electrical power.

Figure 4:
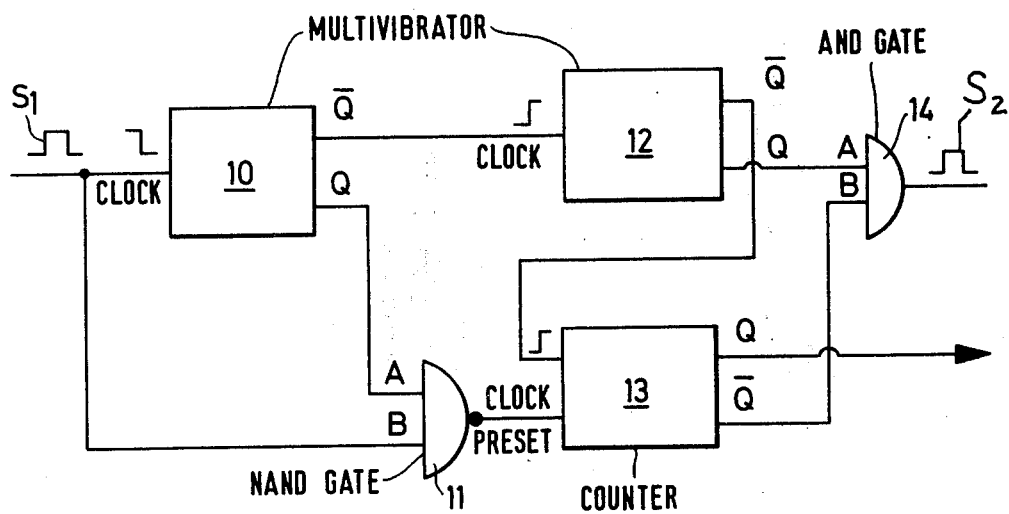
FIG. 4 shows a block diagram of one embodiment of the interference detector device shown in the FIG. 3.

FIG. 4 is a block diagram of one embodiment of the interference detector 3. A retriggerable monostable multivibrator 10 is coupled to a NAND gate 11 and a monostable multivibrator 12. A counter 13 in the form of a "flip flop" is coupled to the NAND gate 11 and the multivibrator 12. An AND gate 14 is coupled to the multivibrator 12 and the counter 13.

The operation of the circuit is as follows:

Assume that a trigger signal $S_1$ (the above mentioned first signal) is generated by an incoming IEKG signal. This results in a logical high at the input terminal of the multivibrator 10. The multivibrator 10 remains in a stable state since it is triggered by the trailing edge. The output terminal of the NAND gate 11 retains a logical high, since the input terminal A is a logical low. Only when the signal $S_1$ changes from its logical high to its logical low will the multivibrator 10 change from its state of rest to its operating state, so that its output terminal Q will become a logical high. In correspondence, a logical high will appear at the input terminal A of the NAND gate 11. The input signal at the input terminal B, however, changes to its logical low, so that the output terminal of the NAND gate 11 remains at a logical high, due to the delay of the signals in the multivibrator 10.

Thus, the counter 13 does not change its state as a result of a non-repetitive signal. If no additional trigger signal is sensed during the monitoring period $Z_{\ddot{U}}$, the duration of which is determined by the multivibrator 10, then the multivibrator 10 returns to its state of rest and sets the multivibrator 12 into action. The multivibrator 12 delays incoming signals so that the resetting of the counter 13 does not take place at the same time as the operation of the AND gate 14. Generally, the multivibrator 12 could include an RC unit.

When the counter 13 remains in a state of rest, its $\bar{Q}$ output terminal which is connected to the input terminal B of the AND gate 14 remains at a logical high. Any signal at the output terminal Q of the multivibrator 12 is coupled through the AND gate 14 (input terminal A) to the output terminal of the circuit forming the second signal $S_2$ which initiates the second period of time $Z_E$.

When the monostable multivibrator 10 is in its operating position, the occurrence of a further trigger signal results in the following: the monostable multivibrator 10 is retriggerable so that a further trigger signal will extend its time interval by one monitoring period without allowing it to return to its state of rest. In addition, the further trigger signal changes the output terminal of the NAND gate 11 from a logical high to a logical low because a logical high is being applied to both input terminals A and B of the NAND gate 11. As a result of this, the counter 13 changes its state so that a logical low is applied to the input terminal B of the AND gate 14. If no further trigger signal occurs, then the monostable multivibrator 10 will return to its state of rest after a time period of one monitoring period $Z_{\ddot{U}}$ subsequent to the occurrence of the last trigger signal. This action sets the multivibrator 12 into action.

Due to the operating condition of the counter 13, the output terminal $\bar{Q}$ of the counter 13 is applied to the input terminal B of the AND gate 14 to produce a logical low, so that no signal is conducted any further by the multivibrator 12. When the monostable multivibrator 10 changes from its operating state to its state of rest, then the counter 13 is reset via the CLOCK input of the counter 13 by the trailing edge of the signal at the output terminal $\bar{Q}$. The entire circuit is again in its original state.

Either the output terminal Q or the output terminal $\bar{Q}$ of the counter 13 can be used to indicate the presence of an interference signal. These output terminals can be used to adjust or increase the operating frequency of the pacemaker.

If more than two trigger signals occur within the monitoring period $Z_{\ddot{U}}$, the mode of operation remains the same as in the case of two trigger signals not so occurring except that the monitoring period is extended by a time period of one monitoring period.

The circuit described herein can be used in connection with unipolar as well as bipolar stimulation electrodes. It is known, however, that unipolar stimulation electrodes are generally more susceptible to the coupling of interference signals than the bipolar electrodes. Thus, the instant invention is particularly advantageous for use in connection with unipolar stimulation electrodes.

We wish it to be understood that we do not desire to be limited to the exact details of construction shown and described, for obvious modifications will occur to a person skilled in the art.

Having thus described the invention, what we claim as new and desire to be secured by Letters Patent, is as follows:

1. A heart pacemaker for generating a heart stimulation signal in the apparent absence of any heart stimulation signal during a given duration of time, comprising, in combination:

interference detecting means operable for sensing intracardiac voltage signals possessing predetermined voltage waveform properties and operable for generating, respectively, first and second signals; said interference detecting means including a retriggerable monostable first multivibrator responsive to a trigger signal and operable for determining a first period of time, a NAND gate coupled to said first multivibrator, coupled to said trigger signal, a second multivibrator coupled to said first multivibrator and operable for initiating a second period of time, a flip flop device coupled to said NAND gate and said multivibrator and responsive thereto, and an AND gate coupled to said second multivibrator and said flip flop and operable for generating one of said second signals, thus inhibiting said heart stimulation signal, said first signal being generated in response to the sensing of one of said intracardiac voltage signals by said detecting means, and one of said second signals being generated whenever one of said voltage signals is not succeeded by another voltage signal during said predetermined first period of time; and generating means coupled to said detecting means and operable for generating said heart stimulation signal at the completion of said predetermined second period of time subsequent to the occurrence of one of said second signals and operable to have said second period of time interrupted in response to the occurrence of a further one of said second signals.

2. The heart pacemaker as claimed in claim 1, wherein said first period of time is from about 25 miliseconds to about 200 miliseconds.

3. The heart pacemaker as claimed in claim 1, wherein said first period of time is from about 120 miliseconds to about 150 miliseconds.

* * * * *